United States Patent [19]

Baskins et al.

[11] Patent Number: 4,549,080
[45] Date of Patent: Oct. 22, 1985

[54] DOUBLE-PASS FLUE GAS ANALYZER

[75] Inventors: Lowell L. Baskins, Santa Barbara; James M. Keene, Ojai; John G. Montfort, Santa Barbara, all of Calif.

[73] Assignee: Infrared Industries, Inc., Santa Barbara, Calif.

[21] Appl. No.: 505,387

[22] Filed: Jun. 17, 1983

[51] Int. Cl.$^4$ .............................................. G01J 1/00
[52] U.S. Cl. ..................................... 250/343; 250/338
[58] Field of Search ................ 250/343, 339, 353, 338

[56] References Cited

U.S. PATENT DOCUMENTS

| 3,448,267 | 6/1969 | Blythe et al. | 250/353 |
| 3,968,367 | 7/1976 | Berg | 250/343 |
| 4,013,260 | 3/1977 | McClatchie et al. | 250/343 |
| 4,233,513 | 11/1980 | Elder et al. | 250/343 |
| 4,297,577 | 10/1981 | Coe et al. | 250/343 |

FOREIGN PATENT DOCUMENTS

| 1000070 | 11/1976 | Canada | 250/343 |
| 2350479 | 4/1975 | Fed. Rep. of Germany | 250/343 |
| 2720636 | 9/1978 | Fed. Rep. of Germany | 250/343 |

Primary Examiner—Alfred E. Smith
Assistant Examiner—Richard Hanig
Attorney, Agent, or Firm—Harry W. Brelsford

[57] ABSTRACT

A mixture of $H_2O$, $CO_2$ and CO are measured in the same sample chamber by infrared radiation passing through the chamber and absorption filters passing a narrow band in their respective absorption curves to an infrared detector. Background radiation is zeroed by grounding the detector response when an opaque segment is disposed in the path. A reference filter detects drift which is automatically corrected.

8 Claims, 7 Drawing Figures

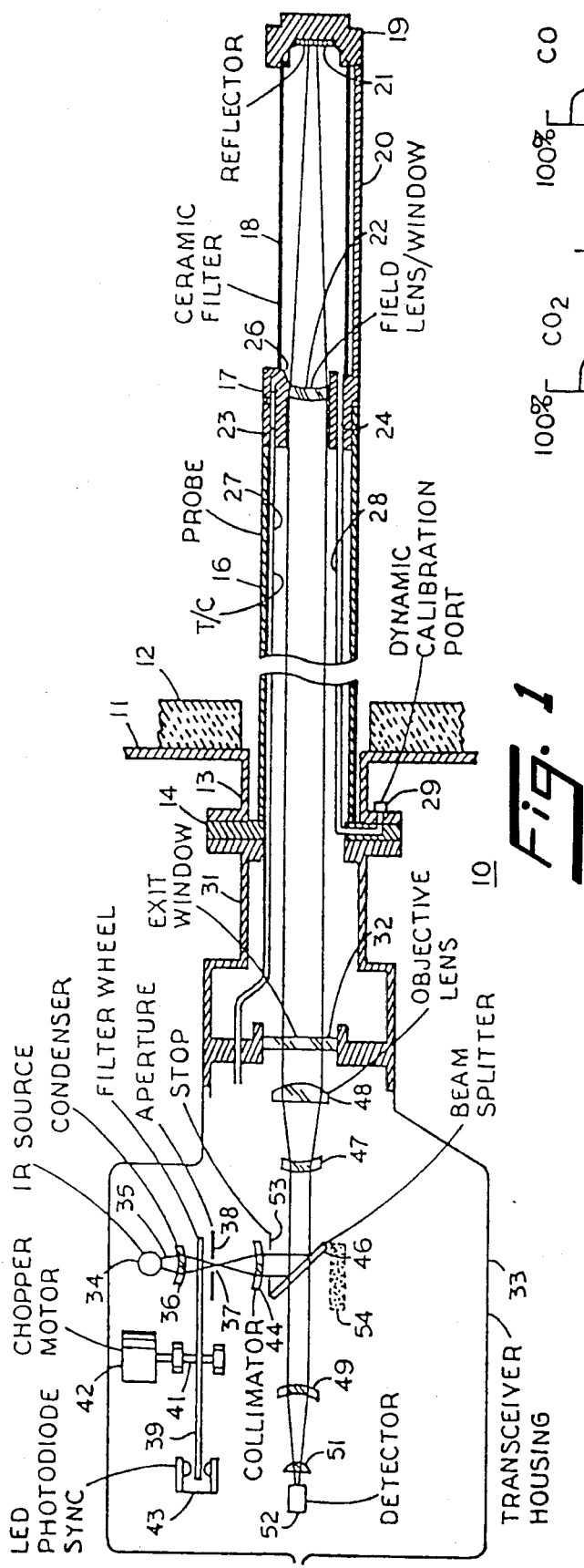
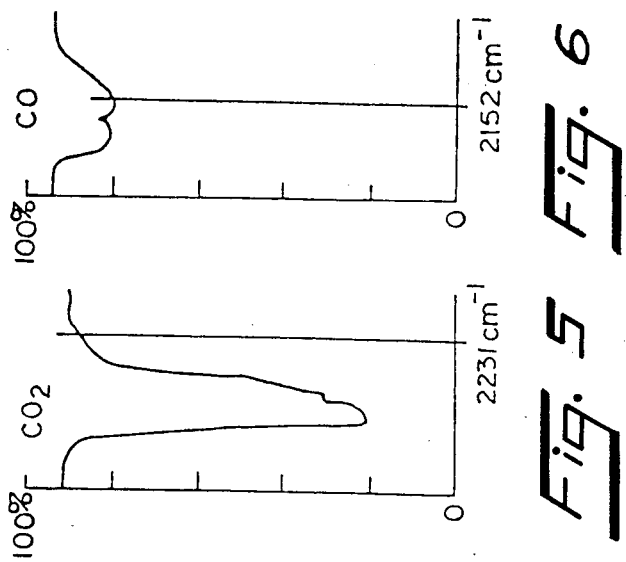
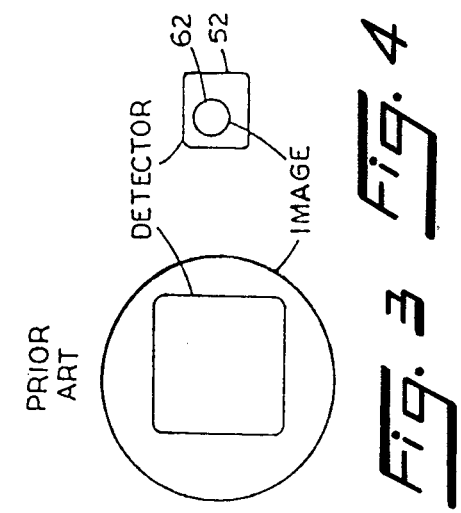
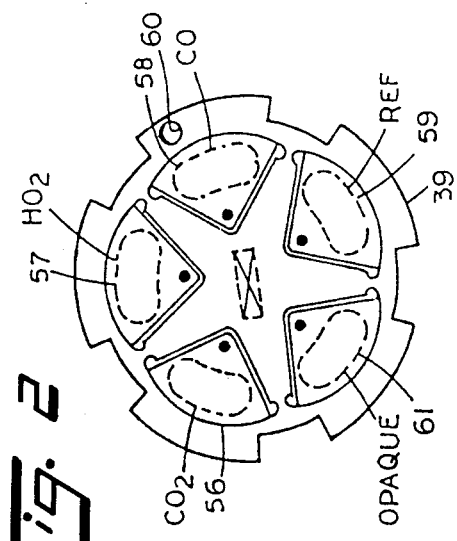

DOUBLE-PASS FLUE GAS ANALYZER

TECHNICAL FIELD

This invention relates to flue gas analyzers for the stacks of industrial furnaces in order to obtain the most efficient burning of hydrocarbon fuels using atmospheric oxygen.

BACKGROUND OF INVENTION

This invention relates generally to a gas analyzer for the control of the combustion process involving oxygen and the combustible elements of hydrocarbon fuels. The usual source of oxygen is air which contains approximately 1 part oxygen and 4 parts nitrogen. If too much air is supplied in the burning process heat must be expended to raise the temperature of the excess oxygen and nitrogen molecules to the stack temperature. Too little air results in a "fuel rich" combustion with the appearance of hydrogen and carbon monoxide in the flue gases, with a consequent waste of fuel. Good combustion control is achieved by the careful control of the concentration of oxygen ($O_2$), carbon dioxide ($CO_2$), and carbon monoxide (CO) in the flue gases. In practice the objective is to obtain combustion that is just slightly "fuel lean".

If only one gas is monitored the choice is $O_2$ or CO. However in most industrial situations where a high premium is placed on the minimum loss of heat up the stack, the concentrations of two of the three gases are determined for the control process. Early measurement systems used extractive analyzers where the gases were analyzed away from the problems of heat and vibration of the boiler and stack. Careful sampling techniques were required to preserve the integrity of the sample as it was transported from the stack to the point of measurement. However the delay of several minutes between the time of the sample extraction in the stack until the data could be supplied for change of control conditions led to the development of the in-situ CO monitor based on the principle of selective absorption of the CO molecule in the infrared spectrum.

An attempt is made in all infrared analyzers to select a spectral interval of frequencies which provides a good match of the source/detector characteristics and the spectral absorption curve of the gas. Ideally the instrument should not respond to any other gas which may be in the sampling region. Unfortunately these conditions are seldom realized and particularly in the case of carbon monoxide which must be measured at low concentrations (about 100 ppm), high concentrations of interfering water vapor and carbon dioxide are always present in the stack. The combustion of hydrogen and oxygen and carbon and oxygen causes water vapor and carbon dioxide to be present. Reasonably low levels of the $CO_2$ interferent may be achieved with a spectral filter having a very low transmittance in the wings of the filter. Water vapor absorption in the CO band, however, can be as large as the CO absorption at elevated stack temperatures (200 C.). The gas filters (transparent gas filled cells) used in some instruments provide a better match of the gas absorption spectral lines than optical filters but they also suffer from interference by $CO_2$ and $H_2O$.

Insufficient attention to the large variation in the absorptivity of a gas with temperature and to a lesser extent pressure has been given in present day in-situ analyzers. The spectra of any gas which absorbs in the infrared consists of a progressive series of lines at fixed or constant spectral frequencies. The width of the spectral line is a function of the pressure and temperature but more importantly the absorption strength of each line varies with the temperature and the quantized ground-level energy E of each line. The effect of this variation of E with each line is to reduce the line strengths in the center of the band and to increase the line strengths in the wings of the band as the temperature of the gas species increases. The indicated absorption by carbon monoxide as seen through a filter positioned at the center of the CO gas absorption band will significantly decrease with a rising temperature, i.e. the gas has negative temperature coefficient. The CO when seen through a similar filter with a spectral peak in the wings of the gas band exhibits a positive temperature coefficient. This is the reason the shape of the gas concentration curve is often observed to change in instruments where the filter temperature is not precisely controlled. The spectral peak of the filter varies with its temperature causing a change in the gas curve both in magnitude and shape.

BRIEF SUMMARY OF THE INVENTION

We have discovered that CO and the interfering gases $CO_2$ and $H_2O$ can be measured simultaneously in-situ in a stack. We have devised a flue gas analyzer having the capability to generate signals proportional to CO concentrates ranging from zero to thousands of parts per million independent of the comparatively high concentrations and absorption strengths of carbon dioxide and water vapor. We have devised microprocessors that can readily handle the data from multiple channels for CO, water vapor and carbon dioxide. With no need to treat a second gas as an interferent, two or three gases in spectral proximity are readily detected.

Such a technique requires the concomitant equations and algorithms for the solution of two or three non-linear sets of data. The performance of the analyzer as a system is dependent on the software as well as the hardware. It also follows that because $CO_2$ can be accurately measured, this information can be combined with the CO data to provide a unique solution of the stoichometric air/fuel ratio in controlling the combustion process with a single instrument.

We designate the infrared spectrum in terms of frequency, and not wavelength, by the inverse centimeters designation $CM^{-1}$.

The measurement of all the gases for combustion control with one instrument requires compatibility of the absorption strength of the gases in a common path length. A $CO_2$ filter at 2350 ($CM^{-1}$) wavenumbers has a peak of the absorption band for the $C^{12}$ isotope, but this peak is too strong for a path length long enough to measure 100 ppm of CO. We have found that a sufficient signal can be generated in the C13 isotope region (about 2250 $cm^{-1}$) of the $CO^2$ absorption band. This frequency selection requires a very close tolerance on the temperature control of the filter because the rate of change of absorption of $CO_2$ with wavenumber (which varies with temperature) at the absorption edge of the carbon 13 isotope is very large. The spectral peaks of the filters change with the temperature of the various layers of the materials in the multilayer interference film.

Because the infrared absorption of a gas varies with temperature, the temperature of the stack gas sample must be known. A readout of the gas temperature of a thermometer located in the gas sample chamber in the stack is coupled with an appropriate temperature function for each gas in the microprocessor algorithm to effect a temperature corrected measurement.

We have selected the frequency for the filter for water vapor at a point where there is practically no interference from $CO_2$ or CO. Additionally we have selected this frequency at about the maximum absorption for methane, $CH_4$, and substantial absorption for ethane, propane and butane. This frequency is 3022 $CM^{-1}$ and results in a fairly pure reading for water vapor. We have developed tables for the interference of water vapor in $CO_2$ and CO absorption, and applying the percent of water vapor present, the absorption output for $CO_2$ and CO is corrected. An additional result of this selection is the use of the water vapor absorption as an alarm for the combustible gases of methane, ethane, etc. The normal output for a water vapor channel is relatively constant for a given fuel, and if the output increases over a given tolerance it is used as an alarm for these combustible gases.

Elimination of Stack Particulates

Prior art gas analyzers that direct radiant energy across the interior of a stack have given false readings because the stack particulates intercepted the beam in addition to gases absorbing the beam. For example coal fuel has fly ash particulates that may be entirely lacking if oil is used as a fuel. We have devised our optical path to avoid this problem by incorporating at the outer end of our cantilever probe a hollow cylinder made of porous ceramic material. The pore size is controlled to exclude ash and other particulates. We have found that the ceramic cylinder effectively excludes particulates while maintaining a good flow of stack gases. Further the interior does not become dirty with particulates and the infrared radiation from the hot ceramic is a constant for a given temperature. A mirror is disposed at the far end of the cylinder causing the beam to traverse this cylinder twice. This ceramic cylinder is the sample chamber for the analyzer.

Underfilling the Detector

An in-situ stack gas analyzer is in a very hostile climate with hot stack gases causing uneven expansion of the metal tubes and other apparatus components, especially during start-up. Optical systems disposed in such tubes will have their optical paths distorted. Also the swift passage of stack gases past the probe will often set up vibrations that cause corresponding vibrations of the optical path.

Prior art infrared gas analyzers of all types use an extended or oversize radiating source to ensure that the sensitive area of the detector is completely filled or covered with as much radiant energy as possible. This technique also minimizes the effects of vibration or other small mechanical movements within the optical system. A small displacement of the detector relative to the image of the IR source will result in the detector receiving the same amount of radiant energy unless the source has a very nonuniform radiating surface. The image of the IR source is larger than the detector so that the detector did not "see" the circumference of the source aperture. This technique of a source image larger than the detector is known as "overfilling the detector".

This technique of the prior art was found to be a complete failure for optical systems to carry out the simultaneous measurement of water vapor, carbon dioxide and CO. We have discovered that just the opposite type of source-detector relationship is needed. We have constructed an optical system that results in projecting an image on the detector that is *smaller* than the detector surface. We refer to this technique as "underfilling the detector".

We found only one feasible way to cause an optical system to image an IR source smaller than the detector. This was to provide a stop at the downstream surface of the collimator lens located immediately downstream from the IR aperture and just before the beam splitter. Prior art optical systems known to us used a stop downstream from the objective lens upstream from the detector, but such a position was ineffective for our purposes. Further we found that there must be a complete absence of vignetting.

Background IR Radiation

The filter wheel is heated to maintain filtering frequency stability, and it therefore becomes a source of IR radiation. The wheel rotates and this radiation tends to be modulated, but out of phase with the signal IR. The hot hollow cylinder and the hot metal tubes along the optical path also radiate d.c. infrared radiation. Furthermore the hot gases themselves in the sample chamber are radiating sources of generally uneven radiation. This impressing of an IR component on the a.c. output from the chopper wheel introduces inaccuracies in the readings for our multi-gas analyzer. It became mandatory for us to isolate the unwanted background from the modulated source radiant energy.

We have reduced the radiation from the chopper wheel by placing it within a housing and providing a very small exit aperture for the signal IR from the IR source. We prefer an exit diameter of less dimension than the detector dimension. This expedient did not, however, solve the d.c. radiation problem.

We discovered that making the detector smaller in size had the remarkable effect of diminishing the d.c. background relative to the signal a.c. IR. We have made the sensitive area of the detector about one fourth the size ordinarily used for IR gas analyzers. To accurately focus the very small image of the IR source on this small detector we found it necessary to mount a special field lens on the sapphire window of the detector. The entire optical path must be of very high quality to effect this result. We have used a detector having a sensitive area, of about 1 mm square and it receives an image of the source that is about 0.7 mm in diameter. Vibration and other distortions of the optical path are tightly controlled so that this image is always within the detector surface.

In addition to reducing the size of the detector we have cooled the detector to further reduce the noise to signal ratio. We therefore provide the detector with a cooler to maintain it at about 0° C. We prefer a thermo electric cooler to achieve this result.

Chopper Reflectance

The radiant energy emanating from the source travels the probe path and returns to the beam splitter where part passes through the beam splitter to the detector and part is reflected by the beam splitter back to the chopper wheel. The chopper wheel reflects this energy and the detector sees this reflectance. This reflectance contributed another source of unwanted energy that introduced errors.

We devised a solution to this problem by creating generally uniform reflecting surfaces on all of the filters. This caused the error to be constant in all of the channels, $CO_2$, CO, $H_2O$ and reference, and in proportion to the signal i.e. a weak signal would reflect a fixed percentage of the signal and a strong signal would reflect the same percentage of the strong signal. In this fashion, filter wheel reflectance was nulled out of the system.

Opaque Filter Wheel Section

While the uniform reflectance of the filters solved the problem generally, there was still the problem of how much background or d.c. infrared was present in each segment of system IR chopped by the chopper wheel. A large d.c. component would obviously give a false reading on a very weak signal. We devised a mechanism for measuring this d.c. component of the chopped signals. We provided a fifth segment in the filter wheel which was opaque. Therefore, any energy received by the detector when the opaque segment was excluding energy from the system IR source, would be due to background or d.c. IR radiation. This reading from the detector output while the opaque section excludes system IR is merely substrated from the detector output for the filter channels to give true readings for their respective gases and the reference.

To make this "opaque" reading even more accurate we have accounted for the background IR that is reflected by the beam splitter to the chopper wheel while the opaque section excludes source IR. This we did by constructing the surface of the opaque section toward the beam splitter with the same reflectance as the filter surfaces. The background IR that reaches the filter wheel is reflected uniformly by each segment of the filter wheel, thus eliminating error.

BRIEF DESCRIPTION OF THE DRAWINGS

Various objects, advantages, and features of the invention will be apparent in the following description and claims, together with the drawings forming an integral part of this specification and in which:

FIG. 1 is a plan view in schematic form and with parts in full section of the optical-mechanical parts of the instrument showing a probe inserted into the stack of an industrial furnace.

FIG. 2 is an elevation view of the filter wheel of FIG. 1.

FIG. 3 is a diagram of the prior art wherein the image projected upon the detector is larger than the detector.

FIG. 4 is a diagram of the relationship of image and detector in accordance with the present invention wherein the detector is about one-quarter of the usual size and wherein the image is smaller than the entire area of the detector.

FIG. 5 is a diagram of the transmittance of $CO_2$ at various frequencies and shows the selection of the filter frequency at the right shoulder of this curve.

FIG. 6 is a transmittance diagram of CO showing the selection of the filter frequency at the maximum absorption point on the curve.

DETAILED DESCRIPTION OF THE INVENTION

Figure 7:
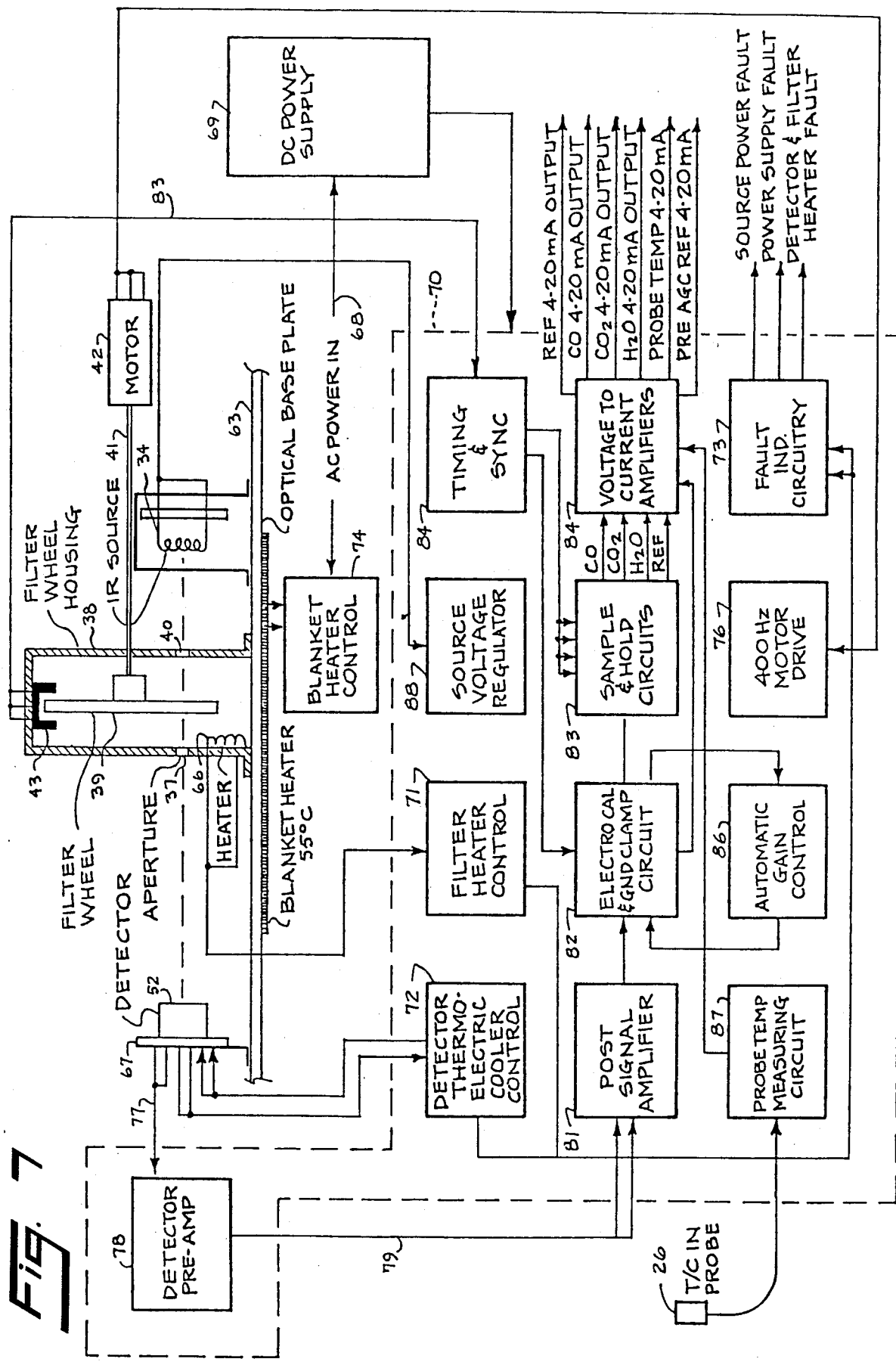
FIG. 7 is a schematic illustration of the source and detector and the filter wheel and showing the various circuits in block diagram that are utilized to project current readouts indicating accurately the concentration of the three gases, CO, $CO_2$, and $H_2O$.

Referring to FIG. 1, which is a plan view of the entire optical-mechanical parts of the analyzer, the analyzer generally is designated as 10. The entire apparatus is secured to a stack 11, which may be lined by a suitable refractory 12. Projecting from the outer left surface of the stack 11 is an annular flange 13 to which is secured a probe flange 14 having secured to it a hollow tubular probe 16 of stainless steel or other noncorrosive metal. The probe 16 is inserted into the interior of the stack 11, and the hot gases of combustion flow about it, upwardly with respect to paper of the drawing FIG. 1.

Threaded or otherwise secured to the right end of the tube 16 is a housing 17, which has axially extending fingers 20, which surround a hollow ceramic cylinder 18, which is supported between the base of housing 17 and an end cap 19. The ceramic cylinder is provided particularly in accordance with the invention and is porous in construction to allow flue gases to flow through it. The pore size is carefully selected to exclude particulates such as fly ash, but still admit a ready flow of gases.

The housing end piece 19 also retains a mirror 21, and the inner end of the housing 17 retains a combined field lens and window 22. The window 22 and the end piece 19 close off the two ends of the ceramic cylinder 18, so that the cylinder 18 becomes the sample chamber for the analyzer 10.

Disposed in the base of the housing 17 are two passages 23 and 24. Passage 23 retains a thermocouple 26 exposed to the hot gases in the cylinder to measure the temperature of the hot gases. Wires 27 lead from the thermocouple 26 to the left in FIG. 1. The other passage 24 is connected to a tube 28 connected to probe flange 14 and terminates at a fitting 29. This tube 28 is used, if needed, for field calibration in situ and permits gases of known concentration to be flowed into the ceramic cylinder 18 to calibrate the instrument. Such gases are available from the National Bureau of Standards.

Referring now to the left end of FIG. 1, secured to the flanges 13 and 14 is a housing 31, which retains an exit window 32. Secured to the left end of housing 31 is a transceiver housing 33. Disposed in the housing 33 are the various components that complete the optical-mechanical apparatus of the invention. A source 34 passes infrared radiation 35 to a condenser lens 36, which focuses the energy into a small aperture 37 in an opaque member 38. We presently prefer an aperture about 0.7 mm in diameter. In actual practice, as shown in FIG. 7, the opaque member 38 is a housing surrounding a filter wheel. Before the infrared reaches the aperture 37, it passes through successive filters (shown in FIG. 2) in a chopper wheel or filter wheel 39 mounted on a shaft 41 rotated by a motor 42. Disposed at the left edge of chopper wheel 39 is a LED photodiode 43 that generates a signal for each filter wheel segment as the rotation of the wheel interrupts a light beam. In this fashion, the electronic output of the system is keyed or synchronized to the various filters as they are disposed in the beam of radiation 35.

After the radiation passes from the aperture 37 it impinges upon a collimator lens 44, which aligns the radiation in parallel rays. The radiation thereafter strikes a beam splitter 46, which directs part of the radiation to the right to pass through a beam expander lens 47, an objective lens 48, the window 32, the field lens 22 to the mirror 21, where it is reflected back along the same path to the beam splitter 46. Part of the reflected radiation is directed by the beam splitter up to the collimator lens 44 and from there up to the filter wheel 39. The other part of the reflected infrared passes through the beam splitter 46 to receiving lens 49 and then to a small field lens 51 disposed close to an infrared detector 52. In actual practice the field lens 51 is placed on the sapphire face of the detector 52 to obtain the very small image as explained previously.

Referring back to the collimator lens 44 and the beam splitter 46, there is provided particularly in accordance with the invention a stop 53 disposed between these two optical elements. We found that this is the only feasible location of an optical stop to create a small image of the source 34 that is smaller than the very small sensitive area (about 1 mm square) of the detector 52.

Referring back to the beam splitter 46, it will be apparent that part of the radiation from the source 34 will pass through the beam splitter and, if not controlled, will heat up the transceiver housing 33 and become a source of d.c. infrared. We avoid this problem by placing flock 54 or other IR absorbent 54 on the far side of the beam splitter.

FIG. 2

Referring to FIG. 2, the filter wheel 39 is shown in elevation. There it will be noted that there are five segments, including four filters: filter 56 for $CO_2$, filter 57 for $H_2O$, filter 58 for CO, and reference filter 59. The fifth segment contains an opaque material 61 that stops all radiation. The filters and the opaque section 61 are so constructed that the surface toward the beam splitter 46 (FIG. 1) has approximately the same reflectance to infrared radiation. We presently prefer to construct our multilayer filters to have the following frequencies and band widths:

| | | |
|---|---|---|
| $CO_2$ | 2230 cm$^{-1}$ | 40 cm$^{-1}$ |
| CO | 2152 cm$^{-1}$ | 38 cm$^{-1}$ |
| $H_2O$ | 3022 cm$^{-1}$ | 54 cm$^{-1}$ |
| Reference | 2600 cm$^{-1}$ | 50 cm$^{-1}$ |

The $H_2O$ and reference frequencies are selected from a part of the spectrum that is substantially free from interference by CO and $CO_2$. A hole 60 in the rim indexes the sync 43 to the CO segment.

FIGS. 3 AND 4

Referring now to FIGS. 3 and 4, FIG. 3 shows the usual relationship of detector size to source image wherein the diameter or dimension of the image is much greater than the detector size. Such a relationship accommodates much movement between detector and image caused by temperature distortion of the probe, vibration, drift, aging, and other effects and is the relationship customarily used in stack gas analyzers. FIG. 4 illustrates our discovery that an image 62 must be smaller than the sensitive part of the detector 52 in order to obtain an operative optical system for our multigas analysis technique. In practice we use a detector area about 1 mm square and an image of about 0.7 mm in diameter.

FIGS. 5 AND 6

Illustrated in FIG. 5 is the transmittance curve for $CO_2$ often referred to as the absorption curve. The ordinate is in percentage of transmission, and the abscissa is frequency. There it will be noted that there is a very sharp drop in transmission, but we deliberately avoid this very strong absorption zone to select our $CO_2$ filter frequency at 2230 cm$^{-1}$. This is located on the right shoulder of the curve at a point of low infrared absorption.

FIG. 6 illustrates the percentage transmission for CO, and on this curve we select the maximum available absorption point on the curve 2152 cm$^{-1}$. The reason for this is that very little CO is present, and CO is measured in parts per million, whereas $CO_2$ is measured in percentages as high as twenty percent. By selecting a low response frequency of the $CO_2$ and a high response frequency for CO, we generally equalize the output for the detector 52. This avoidance of great contrasts gives more accurate readings for both gases.

FIG. 7

FIG. 7 is a diagram of the electrical and some electronic components of the system in order to create electrical currents that may be utilized by a microprocessor to automatically calculate the percentage of $H_2O$ vapor, $CO_2$ gas, and CO gas continuously on a real time basis.

Some of the parts of the instrument previously identified are shown in elevation at the upper part of FIG. 7 whereas in FIG. 1 they were shown in plan. The filter wheel 39 is disposed in the housing 38 in which is disposed the exit aperture 37. A window 40 in housing 38 permits infrared radiation from the source 34 to enter the housing to be intercepted by the filter wheel and to exit at aperture 37 and after traversing the optical path to impinge upon the detector. The filter wheel motor 42, the filter wheel housing 38, and the detector 52 are all mounted on an optical base plate 63 in order to maintain exact mechanical alignment of the various components located in the transceiver housing 33 of FIG. 1. In practice, the transceiver housing is closed and the base plate 63 is heated to a temperature of 55° C. by a blanket 64 disposed on the underside of the plate. The filter wheel housing 38 is independently heated to 70° C. to maintain the frequency stability of the filters 56, 57, 58, and 59, as mentioned previously. Housing 38 has a heater 66 for this purpose.

We prefer to continuously purge the transceiver housing 33 and the probe between windows 32 and 22 by flowing through them dry air devoid of CO and $CO_2$ or by using dry nitrogen.

As mentioned previously, in order to reduce the noise-to-signal ratio, the detector 52 is cooled to 0° C., and this is done by a thermoelectric cooler indicated schematically by element 67.

Considering now the electrical circuit, at the right side of FIG. 7 an a.c. power source 68 supplies power to a d.c. power supply 69, which in turn distributes d.c. power to all the elements within the broken lines 70, including a filter heater control 71, a detector thermoelectric cooler control 72, and a fault indicator circuit 73. A blanket heater control 74 is also supplied with a.c. power.

The output of the detector 52 is delivered by wires 77 to a detector preamplifier 78, and its output is delivered by wires 79 to an amplifier 81, which delivers its output to an electrocalibration unit 82 that modulates the detector output a known amount. This electrocalibration circuit also establishes an electrical ground for the pulse signal from the opaque channel (section 61) from the detector so that a true height or voltage will be established for the other channels. The LED photodiode sync 43 delivers its sync signals through a wire 83 to a timing and sync element 84, which in turn delivers a signal to the electrocalibration unit 82 for the opaque channel and delivers sync signals for the four filter channels to circuit 83. In this fashion, the circuit 83 identifies the detector reading with the proper filter 56, 57, 58, and 59.

The electrocalibration unit circuit 82 delivers its output to sample and hold circuits 83. This circuit receives the signal from each filter and holds the signal until the revolution of the filter wheel is completed and the same filter response is again repeated. The sampling aspect of this circuit is to measure the voltage of each signal from the respective filter elements.

The measured voltages of the pulses from circuit 83 could be delivered directly to a microcomputer, but we prefer to convert these voltages into currents in the range of four to twenty milliamperes. This conversion of voltage to amperes is performed in circuit 84, and the outputs are labeled in this 4 to 20 ma range.

The function of the reference filter 59 (FIG. 2) is to establish an electrical reference to which the output of the other filters may be compared. This reference filter frequency is little affected by $H_2O$, $CO_2$, or CO. The pulse output of this reference should remain constant, and, if it varies, this indicates that the amplification of the other filter responses is changing. The response of the reference filter is delivered by circuit 82 to an automatic gain control circuit 86. If the voltage of the reference pulse exceeds a selected norm (for example, 8 volts), then a correction currrent is supplied to circuit 82 to correct all the amplitudes of the other pulses. Vice versa, if the reference pulse does not reach the norm, then an opposite correction is made.

The output must also be corrected for temperature of the gases in the ceramic sample chamber 18 (FIG. 1), because the absorption of IR varies with temperature. The thermocouple 26 (lower left in FIG. 7) delivers its output to a measuring circuit 87, which in turn delivers its output to the voltage-to-current amplifier to correct that output and give a more accurate reading.

Also incorporated in the circuit of FIG. 7 are fault indicators that reveal faults in the important areas of source power supply, detector cooler supply, and filter wheel housing heater supply. This is the function of the fault indicator circuit 73. Any changes in these power supplies would result in false measurements and must be corrected.

Also shown in FIG. 7 is a power supply 88 for the IR source 34. This supply carefully regulates the current to the IR source 34, so that it will maintain a constant temperature.

Electronic Spanning

The outputs of our analyzer can be calibrated by standard concentrations of gases such as those obtained from the National Bureau of Standards. However, our apparatus can be spanned, or calibrated, electronically, because of the use of the reference filter 59 and the control of the system by the automatic gain control circuit 86. This results because the reference filter signal is independent of CO and $CO_2$, being out of the absorption curves for these gases. Since the output signal for a particular channel represents the response of more than one gas, an electrical gain change of one channel affects the indicated concentration of all gases unless the new gain is recognized. This is the function of the automatic gain control 86.

At the time of factory calibration of the analyzer, the electrical gains are set. The electrical signals of block 86 establish the fundamental constant of proportionality between the percent modulation of the signal and the signal voltage. Means are provided for automatically verifying these constants at any time so that one can be assured that ten percent modulation of the input signal, for example, always yields the same voltage at the output. This is done by comparing the reference output of block 84 to the reference output before automatic gain control, the top and bottom outputs from block 84. Slight changes in the response of both the primary gas and the secondary gases can be accommodated in the software, but normal operation of the system depends principally on stability of the electrical signals and spectral control exercised with analyzer hardware.

UTILIZATION OF ELECTRICAL OUTPUTS TO OBTAIN CONCENTRATION READOUTS

This step-by-step description is used to convert the electrical outputs of block 84 (FIG. 7) to useful readouts of gas concentration. Basically the three signals fed from the present invention to a control unit as 4 to 20 ma currents are converted to digital signals for the data processing by an Intel microprocessor. In the ensuing discussion the signals are identified with the $H_2O$, $CO_2$, and CO channels although, except for the water channel, these signals are a composite of the responses to three gases. The specificity of the water channel is not a requirement to solve the problem of conversion from gas modulation to gas concentration. However the solution is easier and faster if the $H_2O$ signal can be attributed only to water vapor. We have carefully designed the water filter at 3022 $cm^{-1}$ and this makes it possible to preclude any significant interference from $CO_2$ (CO is not a problem). This is the approach in the present invention. It is also pointed out that all signals are non-linear with respect to both concentration (absorber content) and temperature although the departure of water vapor from non-linearity is not severe.

The method described here is an iterative process wherein two correction factors are applied in each cycle through the procedure to ensure a rapid convergence to the final result. The CO channel correction factor is defined as C1 and the corresponding factor for the $CO_2$ channel as C2. The calculation of modulation (proportional to the DC current) for a given gas and gas absorber content and temperature is denoted as $M=M(w)$ where the function $M(w)$ is the gas model which applies to the particular gas. Similarly the calculation of absorber content is denoted by $w=w(M)$ where M is the given modulation and $w(M)$ is the inverse of the gas model equation. The concentration for $H_2O$ and $CO_2$ is displayed as mol percent. CO is displayed as ppm (parts per million by volume). After a division of the absorber content, w by the gas path length the conversion to concentration is a simple ideal gas adjustment for the local pressure and gas temperature. Since water vapor is handled in the equations in terms of vapor density its molecular weight is needed in the conversion to mol percent concentration.

At the end of each cycle the modulations as calculated using the estimated w's are compared with the modulation reported by the analyzer. If the difference of the two values of M (modulation) for any one of the three gases is greater than a predetermined error a portion of the cycle is repeated. This process is continued until the error criteria are satisfied. The tolerances or allowable errors must be small enough to yield the specified accuracy of the measurement.

The procedure for calculation of the $H_2O$, $CO_2$, and CO gas concentrations will now be described. It should be understood any reference to "channel" means the electrical signal, or more specifically the modulation of the gas with respect to the zero reading in the indicated channel. The notation for these instrument output signals is $S(H_2O)$, $S(CO_2)$, and $S(CO)$ respectively.

Step 1: Set C1 and C2 to unity. Determine the magnitude of the error which will be permitted for each signal when compared to the calculated values. Let the error for the $H_2O$ channel be denoted as $E(H_2O)$. Similarly the errors for the $CO_2$ and CO channels are $E(CO_2)$ and $E(CO)$ respectively.

Step 2: Because there is no interference from $CO_2$ and CO in the $H_2O$ channel the concentration of $H_2O$ may be obtained immediately by calculation of
w = w(M)
M = instrument signal in $H_2O$ channel Step 3: With the knowledge of the $H_2O$ concentration derived in Step 2 the modulation attibutable to water in the $CO_2$ channel may now be calculated as
M = M(w)
w = $H_2O$ concentration derived in Step 2
Let M3 = M because this quantity which is the signal due to $H_2O$ in the $CO_2$ channel will be required in the steps to follow. This parameter is calculated only one time.

Step 4: Extract the $H_2O$ signal from the $CO_2$ channel and multiply result by correction factor. Assign the result to the variable S1 ($CO_2$).
S1 ($CO_2$) = (S($H_2O$) − M3)C2

Step 5: If this is the first time through the procedure go to Step 6 otherwise on succeeding iterations go to Step 10.

Step 6: In a manner similar to Step 2 and with a knowledge of the $H_2O$ concentration the modulation attributable to water in the CO channel may be calculated as
M = M(w)
w = $H_2O$ concentration derived in Step 2

Step 7: Extract the $H_2O$ signal from the CO channel and assign result to the variable S1(CO).
S1(CO) = S(CO) − M where M is from Step 6

Step 8: Interference of $CO_2$ in the CO channel in the present invention is less than interference of CO in the $CO_2$ channel, therefore as an interim calculation assume the signal in the CO channel (after the extraction of water in Step 7) is due to CO alone. Now calculate a first estimate of the CO concentration and assign the result to W(CO).
w = w(M)
M = S1(CO) from Step 7
W(CO) = w Step 9: With the estimated CO concentration the CO signal in the $CO_2$ channel may be calculated. Assign the results to the new M9 for later use. This parameter is calculated only one time.
M = M(w)
w = CO concentration from Step 8
M9 = M Step 10: Subtract the signal found in Step 9 from the $CO_2$ water-free signal developed in Step 4 to extract the CO signal. The result is an estimate of the pure $CO_2$ signal.
M = S1($CO_2$) − M9
S1($CO_2$) from Step 4
M9 from Step 9

Step 11: The modulation developed in Step 10 may be used to calculate the $CO_2$ concentration. Assign the concentration to the variable W($CO_2$).
w = w(M)
M = modulation found in Step 9
W($CO_2$) = w Step 12: The $CO_2$ concentration W($CO_2$) is now used to refine the estimate of the pure CO signal. Calculate the $CO_2$ modulation in the CO channel and assign the result to S2(CO).
M = M(w)
w = W($CO_2$) from Step 11
S2(CO) = M Step 13: Extract the residual $CO_2$ signal from the estimated CO signal determined in Step 7 and multiply result by correction factor for CO.
M = (S1(CO) − S2(CO))C1
S1(CO) from Step 7
S2(CO) from Step 12

Step 14: Take the last estimate of CO modulation and calculate the second estimate of CO concentration. Assign result to W(CO).
w = w(M)
M = modulation found in Step 13
W(CO) = w Step 15: The gas concentrations of the three gases have now been calculated and assigned to the variables W(HO), W($CO_2$), and W(CO). Using these quantities (strictly speaking the units are "absorber content" as defined above instead of concentration), the modulation as a function of W is calculated for each gas. The results should then be assigned to the variables T($H_2O$), T($CO_2$), and T(CO) where T denotes the estimated modulations which will later be compared to the instrument modulations S.
M = M(w)
w = W($H_2O$)
T($H_2O$) = M (Estimate for $H_2O$)
M = M(w)
w = w($CO_2$)
T($CO_2$) = M (Estimate for $CO_2$)
M = M(w)
w = w(CO)
T(CO) = M (Estimate for CO)

Step 16: Compare the estimated modulations with the instrument values. Subtract T from the corresponding S and form the absolute value for each gas. This result is then compared with the allowable error E. The next step is as shown below:
If ABS (S($H_2O$) − T($H_2O$)) < E($H_2O$) then continue this Step; otherwise to the Step 17.
If ABS (S($CO_2$) − T($CO_2$)) < E($CO_2$) then continue this Step: otherwise go to Step 17.
If ABS (S(CO) − T(CO)) < E(CO) then continue this Step; otherwise go to Step 17.
GO TO STEP 18

Step 17: Adjust the correction factors by multiplying each current factor by the appropriate quotient (S/T). Next reassign the result to C1 or C2 as the case may be.
C1 = C1*(S(CO)/T(CO))
C2 = C2*(S(CO2)/T(CO2))
GO TO STEP 4

Step 18: Convert the absorber content in the W variables to mol percent concentration for $H_2O$ and $CO_2$ and ppm for CO.

Step 19: END OF PROCEDURE

Presently Preferred Quantities

We presently prefer to operate our apparatus in the following parameter range.

| PARAMETER | PARAMETER RANGE |
| --- | --- |
| Temperature | 20 to 200C |
| Pressure | .7 to 1.0 Atm |
| $H_2O$ Concentration | 2 to 20 Mol percent |
| $CO_2$ Concentration | 2 to 20 Mol percent |
| CO Concentration | 0 to 5000 ppm |

We have designed the optical-mechanical part of our analyzers to hold to an accuracy of plus or minus 1%. The filter frequencies are selected at 30° C.:

| | |
| --- | --- |
| $H_2O$ | 3022 |
| $CO_2$ | 2230 $cm^{-1}$ |
| CO | 2152 $cm^{-1}$ |
| Reference | 2600 $cm^{-1}$ |

The temperatures are as follows:

| | |
| --- | --- |
| chopper wheel housing 38 (FIG. 7) | 70° C. ± 1° C. |
| detector 52 PbSe | 0° C. |
| optical baseplate | 55° C. |
| IR Source 34 | 825° C. |

The chopper rotates at 12,000 rpm.
The optical quantities are:

| | |
| --- | --- |
| exit aperture 37 | .7 mm |
| aperture image on detector | .7 mm |
| stop diameter 53 | 8 mm |
| sensitive detector area | 1 mm square |

The probe may project into the flue any given distance and 6 feet has given good results.

We claim:

1. Apparatus for measuring the concentration of each gas in a mixture in a common sample chamber of $H_2O$, $CO_2$, and CO wherein infrared radiation is passed through the sample chamber along a path to impinge upon an infrared detector comprising:
   (a) filters for transmitting a limited band of frequencies in individual absorption bands, one filter for each of $H_2O$, $CO_2$, and CO:
   (b) means for successively projecting the filters into the path;
   (c) and means for measuring the output of the detector as each filter is projected into the path;
whereby the detector output is a measure of the amount of absorption of the individual gases and therefore a measure of the concentration, characterized by the $CO_2$ filter passing a band of frequencies in the absorption curve of the $C^{13}$ isotope to thereby approximate the absorption by CO.

2. Apparatus as set forth in claim 1 wherein the filters operate inside a temperature-controlled housing amd means are provided to control the temperature in the housing within approximately one-and-one-half percent of a selected temperature.

3. Apparatus for measuring the concentration of each gas in a mixture in a common sample chamber of $H_2O$, $CO_2$, and CO wherein infrared radiation is passed through the sample chamber along a path to impinge upon an infrared detector comprising:
   (a) filters for transmitting a limited band of frequencies in the individual absorption bands, one filter for each of $H_2O$, $CO_2$, and CO;
   (b) means for successively projecting the filters into the path;
   (c) and means for measuring the output of the detector as each filter is projected into the path;
whereby the detector output is a measure of the amount of absorption of the individual gases and therefore a measure of the concentration, characterized by the $H_2O$ filter frequency being in a high absorption frequency for methane so that unusual measurements for $H_2O$ will indicate the presence of methane.

4. Apparatus for measuring the concentration of each gas in a mixture in a common sample chamber of $H_2O$, $CO_2$, and CO, wherein infrared radiation from a source is passed through the sample chamber along a path to impinge upon an infrared detector having an infrared sensitive part approximately one mm across and having an electrical output, comprising:
   (a) a filter wheel having band pass filters and disposed in said path;
   (b) means creating a fixed optical stop in said path down stream from the filter wheel;
   (c) and an optical system that impinges an image of the optical stop upon the detector that is smaller than the infrared sensitive part of the detector.

5. Apparatus as set forth in claim 4 wherein the optical system includes a field lens disposed on the detector.

6. Apparatus for measuring the concentration of gas in a mixture in a common sample chamber of $H_2O$, $CO_2$, and CO, wherein infrared radiation from a source is passed through the sample chamber twice by reflection along a path to impinge upon an infrared detector having an IR sensitive part and having an electrical output, comprising:
   (a) a filter wheel having band pass filters for $H_2O$, $CO_2$, and CO;
   (b) means creating an aperture downstream from the filter wheel;
   (c) a lens for concentrating the radiation at the aperture;
   (d) a collimator lens downstream from the aperture;
   (e) an optical stop disposed at the downstream side of the collimator lens;
   (f) a beam splitter downstream from the stop;
   (g) and lenses for directing the reflected beam through the beam splitter and concentrating the radiation downstream from the beam splitter on the detector with an image of the optical stop that is smaller than the infrared sensitive part of the detector.

7. Apparatus as set forth in claim 6, wherein the filter wheel has an opaque section and the surface of the opaque section in the filter wheel facing the beam splitter has approximately the same amount of reflectance.

8. Apparatus for measuring the concentration of each gas in a mixture in a common sample chamber of $H_2O$, $CO_2$, and CO, wherein infrared radiation from a source travels a path through a sample chamber to impinge upon an infrared detector having a sensitive part comprising:
   (a) a housing;

(b) filter wheel disposed in the housing for rotation and having a plurality of band pass filters;
(c) a source of infrared radiation disposed to send radiation through the wheel filters;
(d) an exit aperture in the housing for the infrared radiation after passing through the filters of the filter wheel and having a size smaller than the sensitive part of the detector; and
(e) a condenser lens inside the housing disposed on said path between the filter wheel and the aperture to concentrate the infrared radiation at the aperture.

* * * * *